United States Patent [19]

Barua et al.

[11] Patent Number: 4,855,463

[45] Date of Patent: Aug. 8, 1989

[54] METHOD OF PRODUCING WATER-SOLUBLE GLUCURONIC ACID DERIVATIVES OF VITAMIN A

[75] Inventors: Arun B. Barua; James A. Olson, both of Ames, Iowa

[73] Assignee: Iowa State University Research Foundation, Inc., Ames, Iowa

[21] Appl. No.: 941,637

[22] Filed: Dec. 15, 1986

[51] Int. Cl.$^4$ ............................................ C09D 309/10
[52] U.S. Cl. .................................... 549/417; 536/119
[58] Field of Search ........................ 549/417; 536/119

[56] References Cited

U.S. PATENT DOCUMENTS

| | | | |
|---|---|---|---|
| 1,917,257 | 9/1931 | Harris | 536/119 X |
| 3,281,440 | 10/1966 | Machleidt et al. | 568/824 |
| 4,055,659 | 10/1977 | Gander et al. | 514/549 |
| 4,473,503 | 9/1984 | Barua et al. | 260/408 |
| 4,545,982 | 10/1985 | Takahashi | 549/417 X |

OTHER PUBLICATIONS

Dawson et al., Carbohydrate Research, 85, pp. 121-129 (1980).
Hicks, Proc. Nutr. Soc., 42, pp. 83-84 (1983).
Kirk-Othmer, Encyclopedia of Chemical Technology, 2nd Ed., vol. I, pp. 222-223 (1963).
Barua et al., Biochimica et Biophysica Acta, 757, pp. 288-295 (1983).
Hilgetag et al., Preparative Organic Chemistry, p. 374 (1972).
Streitwieser et al., Introduction to Organic Chemistry, Second Edition, p. 529 (1981).

Primary Examiner—John W. Rollins
Assistant Examiner—W. Catchpole
Attorney, Agent, or Firm—Tilton, Fallon, Lungmus & Chestnut

[57] ABSTRACT

Water soluble glucuronic acid derivatives of Vitamin A, including retinoyl $\beta$-glucuronide and retinyl $\beta$-glucuronide, having in vivo activity comparable to retinoic acid and retinol and methods of their preparation are disclosed.

6 Claims, No Drawings

METHOD OF PRODUCING WATER-SOLUBLE GLUCURONIC ACID DERIVATIVES OF VITAMIN A

The invention described herein was made in the course of work under two grants from Competitive Research Grant, Science and Education Administration, U.S. Department of Agriculture grant no. 84-CRCR-1-1418 and NIH grant no. AM 32793.

BACKGROUND OF THE INVENTION

The glucuronic acid derivatives of retinol and retinoic acid were first obtained as biliary metabolites of vitamin A (Dunagin et al. *Science,* 148: 86–87, 1965; Zachman et al. *J. Lipid Res.* 7: 3–9, 1966; Lippel and Olson, *J. Lipid Res.* 9: 580–586, 1968). The physiological significance of these glucuronides are not known yet, but recent findings of the presence of retinoyl glucuronide in the small intestine (Zile et al. *J. Biol. Chem.* 257: 3544–3550, 1982) and in the liver (McCormick et al. *Biochemistry,* 22: 3933–3940, 1984) suggest that the glucuronides of vitamin A might play some important role in the overall metabolism of vitamin A. Using very small quantities of natural retinoyl glucuronide, it was shown that the compound is biologically more active than retinoic acid in the vaginal smear assay (Sietsema and DeLuca, *J. Nutr.* 112: 1481–1489, 1982), and 30–100% as active as retinoic acid in the rat growth assay (Nath and Olson, *J. Nutr.* 93: 461–469, 1965).

Blindness resulting from vitamin A deficiency is a world-wide public health problem. Vitamin A deficiency occurs when body stores are exhausted and supply fails to meet the body's requirements, either because there is a dietary insufficiency, requirements are increased, or absorption and use are impaired. Vitamin A and all the known derivatives, except the glucuronides, are insoluble in water; they are lipid soluble and are absorbed and transported using a mechanism similar to the one used by lipids. Like all other exogenous and endogenous lipids that enter the gastrointestinal tract, vitamin A requires solubilization into mixed-micellar solutions before efficient absorption can occur (Underwood, in *Retinoids,* vol. 1, p. 281–392, ed. Sporn et al. Academic Press, Orlando, Fla., 1984). With the availability of a water-soluble derivative of vitamin A, the problem of absorption and transport of vitamin A is overcome.

Several retinoids, retinoic acid in particular, have been found very effective in the topical treatment and cure of xerophthalmia and corneal epithelial wounds (Ubels et al. *Current Eye Res.* 4: 1049–1057, 1985). These retinoids being water-insoluble pose significant problems in the formulation of a suitable vehicle for the clinical use. With the availability of water-soluble glucuronide derivatives, the formulation problem is overcome, since these derivatives could be applied as aqueous eye drops.

The first chemical synthesis of retinoyl β-glucuronide was reported by us (Barua & Olson, *J. Lipid Res.* 26: 1277–1282, 1985), and involves a two-step procedure. Retinoyl fluoride was allowed first to react with 6,3-glucuronolactone to produce the 6,3-lactone of retinoyl glucuronic acid, which was then hydrolysed with very dilute alkali to give retinoyl β-glucuronide. The present invention is an improvement over the two-step procedure.

SUMMARY OF THE INVENTION

The present invention provides a method of producing water soluble derivatives of vitamin A. More specifically, it relates to a method of synthesizing retinyl β-glucuronide and a one step method of synthesizing retinoyl β-glucuronide. The desired water soluble derivatives of vitamin A can be synthesized directly from retinoyl fluoride and glucuronic acid at 60% or better yields using a mild alkaline pH and room temperature.

DETAILED DESCRIPTION

The chemical structures of retinol (I) retinyl β-glucuronide (II), retinoic acid (III) and retinoyl β-glucuronide (IV) are shown as follows.

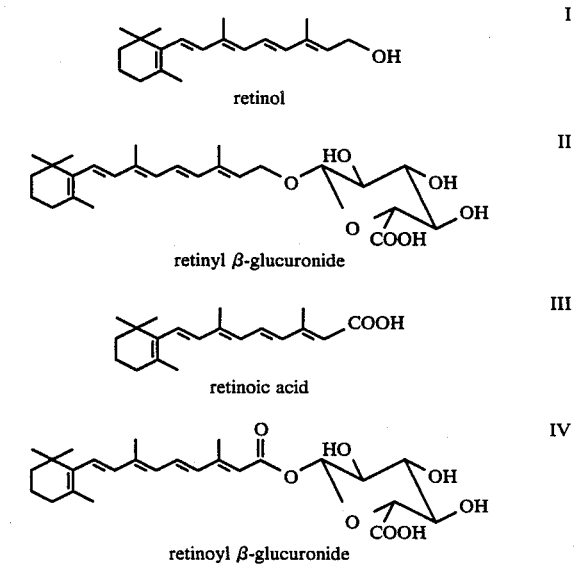

The presence of the glucuronic acid moiety renders the compounds water-soluble.

The starting material for the synthesis of retinoyl β-glucuronide is retinoyl fluoride. Our U.S. Pat. No. 4,473,503 describes the preparation of retinoyl fluoride and is incorporated herein by references. Retinoyl fluoride, unlike most acyl chlorides, is stable in aqueous solution for several days and is hydrolyzed to retinoic acid only on heating in the presence of alkali or acid. It is not appreciably hydrolyzed to retinoic acid even in the presence of bicarbonate at 35°–40° C.

Retinoyl fluoride has the following structure:

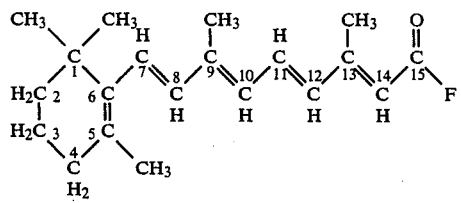

Retinoyl fluoride can be mixed with commercially available glucuronic acid. The reaction is carried out in acetone/water to facilitate the solubility of the water-insoluble retinoyl fluoride and the water-soluble glucuronic acid. The reaction takes place in slightly alkaline pH and hence sodium bicarbonate is used in the reaction mixture. Stirring the mixture at room temperature for 20-24 hours followed by acidification of the solution and extraction with ethyl acetate yields retinoyl glucuronide as the major product. Pure all-trans retinoyl β-glucuronide can be obtained by a combination of column and high-performance liquid chromatography (HPLC).

The starting materials for the preparation of retinyl β-glucuronide include retinol that can be obtained as an oil by saponification of commercially available retinyl acetate, and methyl (2,3,4-tri-O-acetyl glucopyranosyl bromide)-uronate that can be synthesized from commercially available 6,3-glucuronolactone by known procedures (Bollenback et al. *J. Amer. Chem. Soc.* 77: 3310-3315, 1955). The reaction is carried out in the presence of silver carbonate by stirring at room temperature for 20-24 hours. The resulting product is a mixture of unconverted retinol and the fully protected glucuronide of retinol. To obtain the free glucuronide, the crude mixture is saponified without separating the other products and then the products are separated by a combination of column chromatography and HPLC.

Compounds to which this invention relate are useful by reason of their valuable pharmacological properties. The biological activities of retinoyl β-glucuronide and retinyl β-glucuronide were determined with respect to retinoic acid and retinyl acetate, respectively. The glucuronides were found to be comparable in activity to that of retinoic acid and retinyl acetate.

Weanling male rats (Holtzman) were made vitamin A deficient by raising them on a vitamin A deficient diet for 4-5 weeks. When the rats reached weight-plateau stage, they were divided into five groups: Group I received 2.5 μg of all-trans retinoic acid/rat twice daily. Group II received 2.5 μg of all-trans retinoyl β-glucuronide/rat twice daily. Group III received 4.6 μg of all-trans retinyl acetate/rat twice daily. Group IV received 70 μg of all-trans retinyl β-glucuronide/rat/week by intraparetoneal injection. Rats of Group V did not receive any supplement and lost weight at the end of the bioassay period. Rats in the other four groups grew almost at the same rate (Table 1).

TABLE 1

| Biological activity of all-trans retinoyl β-glucuronide | | | | |
|---|---|---|---|---|
| Compound dosed | Amount dosed μg/rat/d | Weight gain g/wk/rat | Biological activity | |
| all-trans retinoic acid | 5.0 | 20.16 ± 3.58 | 100%[1] | 100%[2] |
| all-trans retinoyl β-glucuronide | 5.0 | 17.13 ± 3.50 | 85%[1] | 135%[2] |
| all-trans retinyl acetate | 9.2 | 35.80 ± 10.35 | 100%[1] | 100%[3] |
| all-trans retinyl β-glucuronide | 10.0 | 37.16 ± 4.91 | 104%[1] | 130%[3] |

[1] Based on weight of the compound
[2] Based on retinoic acid equivalent
[3] Based on retinol equivalent The results are, of course, specified merely for the purposes of illustration and, accordingly, are not to be construed as either delimiting or exclusionary. Appropriate dosages in any given instance, of course, depend upon the nature and severity of the condition treated, the route of administration, and the species of mammal involved including its size and any individual idiosyncracies which obtain.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, steric acid, magnesium stearate, magnesium oxide, sodium and calcium salts of phosphoric and sulfuric acid, gelatin, acacia, sodium algenate, polyvinyl pyrrolidone, and/or polyvinyl alcohol, and thus tableted or encapsulated for convenient administration; alternatively, they may be dissolved or suspended in water or comparably in aqueous liquid. Parenteral administration may be effective via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Markin, et al., "Remington's Pharmaceutical Sciences", 14 Ed., Merck Publishing Co. Eaton, Pa. 1956.

The following examples further illustrate the present invention.

EXAMPLE 1

Synthesis of Retinoyl Fluoride

Three grams of retinoic acid was dissolved in 100 ml of warm diethyl ether. The solution was cooled to −70° C. and 1.61 g of N-diethyl-aminosulfurtrifluoride (DAST) dissolved in 5.0 ml of diethylether was added dropwise. (The DAST was supplied by Aldrich Chemical Co., Milwaukee, Wis.) The reaction mixture was warmed to room temperature and the solvent was removed in vacuo. The orange oil was dissolved in 2 ml of hexane and immediately applied to a short column of silica gel (1.5×3 cm; silica gel for dry column chromatography was supplied by Woelm Pharma, Eschwege, W. Germany, and was wet packed with hexane). Retinoyl fluoride which moved as the main orange band was quickly eluted with a mixture of hexane/diethylether (9:1). The solvent was removed to give three grams of oil. Upon dissolving the oil in the minimum volume of hexane, and storing the solution at −20° C., orange-yellow crystals (2.4 g) m.p. 65°–67° C. were obtained: $\lambda_{max}$ 378 nm (hexane), $E_{1\ cm}^{1\%} = 1650$.

EXAMPLE 2

Synthesis of retinoyl β-glucuronide

Retinoyl fluoride (2.4 g) was dissolved in 300 ml of acetone. D-Glucuronic acid (6 g) dissolved in 75 ml of water and sodium bicarbonate (6 g) dissolved in 75 ml of water were added to the retinoyl fluoride solution. The mixture was stirred at room temp. for 12-16 hours. More water (100-150 ml) was added and the stirring was continued for 8-12 hours more until most of the retinoyl fluoride had reacted. The solution was diluted with water, acidified with 1N HCl, and the product was extracted with n-butanol. The extract was washed with water, dried over anhydrous sodium sulfate and then evaporated to dryness in a rotary evaporator. The residue was dissolved in 2-3 ml of diethyl ether and transferred to a silica gel (for dry column chromatography, wet packed with hexane) column. The column was developed with hexane containing diethyl ether (5-50%) to remove retinoic acid and other products. The major yellow band containing retinoyl glucuronide was next eluted with a mixture of $CH_2Cl_2/CH_3OH$ (1:1). The solvent was evaporated to dryness to give solid retinoyl glucuronide (2.1 g, 60%).

An analytically pure sample of retinoyl β-glucuronide was obtained by HPLC of the above preparation on a Whatman ODS-3 column (M9, 50 cm) using methanol/water (7:3) containing 10 mM ammonium acetate at a flow rate of 3 ml/min. Retinoyl β-glucuronide ($t_R$=48.7 min) separated from traces of isomers or anomers ($t_R$=46.4 min). The eluate carrying retinoyl β-glucuronide was diluted with water, made just acidic with 0.1N HCl and the product extracted with ethyl acetate. The extract was washed with water, dried over anhydrous sodium sulfate and then evaporated to dryness. The residue was dissolved in a small volume of diethyl ether and all-trans retinoyl β-glucuronide was precipitated with hexane. The solid was separated and dried. all-trans Retinoyl β-glucuronide:m.p. 142°-143° C. (darkens at 125° C.); $UV_{max}$360 nm ($E_1\,_{cm}^{1\%}$=1065) in methanol and 365 nm in water. The $^1$H-NMR, IR and Mass spectra and C, H analysis results were consistent with the structure. Incubation of retinoyl β-glucuronide with β-glucuronidase (from *E. coli*) in phosphate buffer (pH 6.8) for 0.5-2 hrs. generated retinoic aid.

EXAMPLE 3

Synthesis of retinyl β-glucuronide

Methyl (tri-O-acetyl-α-D-glucopyranosyl bromide)uronate was prepared according to the method of Bollenback et al. (*J. Amer. Chem. Soc.* 77: 3310-3315, 1955). All-trans retinol (4.0 g) was obtained as an oil by saponification of retinyl acetate (4.6 g). To this oil was added methyl (2,3,4-tri-O-acetyl-α-D-glucopyranosyl-1-bromide)-uronate (3.2 g) and silver carbonate (1.5 g). The mixture was stirred in the dark at room temperature for 4-6 hours. Diethyl ether was added and the silver carbonate was filtered off. The filtrate was evaporated to dryness. The residual oil was dissolved in 50 ml of methanol. To this was added 1.5 g of sodium methylate and the mixture was refluxed at 50° C. for 10-15 min. The solution was cooled, diluted with water, acidified with acetic acid, and the product was extracted with n-butanol. The extract was washed with water, dried over sodium sulfate and evaporated to dryness in a rotary evaporator. The residual oil was dissolved in 2-3 ml of diethyl ether and transferred into a silica gel column (silica gel for dry column chromatography was wet packed with hexane). The column was developed with hexane containing 5-50% diethyl ether to remove unconverted retinol and other side products. The column was then developed with 5-10% methanol in dichloromethane when a brownish-red zone was eluted. Development with methanol/dichloromethane (1:1) resulted in the elution of retinyl β-glucuronide as an almost colorless eluate. The fractions showing $UV_{max}$325 nm were pooled, evaporated to dryness to yield a pale yellow powder of retinyl β-glucuronide (2.1 g, 60%). To obtain an analytically pure sample of all-trans retinyl β-glucuronide, the residue was dissolved in methanol and subjected to HPLC on Whatman ODS-3 (M9, 50 cm) column using methanol/water (4:1) containing 10 mM ammonium acetate at a flow rate of 4 ml/min. all-trans Retinyl β-glucuronide was eluted as the major peak at 15 min. The pooled eluates from several chromatography runs were diluted with water, acidified with acetic acid and the product was extracted with ethyl acetate. The extract was washed with water, dried over anhyd. sodium sulfate, and then evaporated to dryness in a rotary evaporator. The residue was dissolved in a small volume of diethyl ether and all-trans retinyl β-glucuronide was precipitated with hexane. The solid was separated and dried. all-trans retinyl β-glucuronide m.p. 138°-140° C. (decom), UV max 325 ( $E_1\,_{cm}^{1\%}$=973) in methanol, 329 ($E_1\,_{cm}^{1\%}$=723) in water. The NMR and mass spectra and C,H analysis results were consistent with the structure.

Treatment of retinyl β-glucuronide with β-glucuronidase (from *E. Coli*) in phosphate buffer (pH 6.8) for 1-2 hours resulted in formation of retinol.

What is claimed is:

1. A method of producing water soluble retinoyl β-glucuronide comprising
   acylating water-soluble glucuronic acid by treatment with water-insoluble retinoyl fluoride, and
   stirring the mixture for an effective amount of time to facilitate the reaction of retinoyl fluoride with glucuronic acid in a mixture of about two parts acetone to about one part water at an alkaline pH of from about 7.2 to about 8,
   acidifying the mixture and extracting the retinoyl glucuronide.

2. The method of claim 1 wherein the mixture is stirred for about 20 to about 24 hours.

3. The method of claim 2 wherein the mixture is stirred at room temperature.

4. The method of claim 1 wherein the mixture is acidified by adjusting the pH of the mixture to about 6 to about 6.8.

5. The method of claim 1 wherein the retinoyl glucuronide is separated to yield retinoyl β-glucuronide.

6. The method of claim 1 wherein the yield of retinoyl glucuronide is about 55 to about 60% based on retinoyl fluoride.

* * * * *